United States Patent
Bayon et al.

(10) Patent No.: US 9,119,898 B2
(45) Date of Patent: Sep. 1, 2015

(54) MEDICAL IMPLANT INCLUDING A 3D MESH OF OXIDIZED CELLULOSE AND A COLLAGEN SPONGE

(75) Inventors: Yves Bayon, Lyons (FR); Sébastien Ladet, Lyons (FR); Olivier Lefranc, Chatillon sur Chalaronne (FR); Philippe Gravagna, Irigny (FR)

(73) Assignee: Sofradim Production (FR)

( * ) Notice: Subject to any disclaimer, the term of this patent is extended or adjusted under 35 U.S.C. 154(b) by 265 days.

(21) Appl. No.: 13/125,595

(22) PCT Filed: Nov. 6, 2009

(86) PCT No.: PCT/IB2009/007742
§ 371 (c)(1),
(2), (4) Date: Jul. 15, 2011

(87) PCT Pub. No.: WO2010/052587
PCT Pub. Date: May 14, 2010

(65) Prior Publication Data
US 2011/0264119 A1    Oct. 27, 2011

Related U.S. Application Data

(60) Provisional application No. 61/112,306, filed on Nov. 7, 2008.

(51) Int. Cl.
*A61F 2/02* (2006.01)
*A61L 27/24* (2006.01)
*A61L 27/20* (2006.01)
*A61L 27/56* (2006.01)

(52) U.S. Cl.
CPC ............... *A61L 27/24* (2013.01); *A61L 27/20* (2013.01); *A61L 27/56* (2013.01)

(58) Field of Classification Search
CPC ........... C08L 1/02; C08L 89/06; A61L 27/56; A61L 27/20; A61L 27/24; A61L 27/48
USPC ................... 606/151; 424/422–426; 623/23.72–23.76
See application file for complete search history.

(56) References Cited

U.S. PATENT DOCUMENTS

| | | | |
|---|---|---|---|
| 5,948,429 A * | 9/1999 | Bell et al. | 424/426 |
| 6,451,032 B1 * | 9/2002 | Ory et al. | 606/151 |
| 2004/0078077 A1* | 4/2004 | Binette et al. | 623/13.17 |
| 2005/0010306 A1* | 1/2005 | Priewe et al. | 623/23.76 |
| 2005/0042250 A1* | 2/2005 | Damien et al. | 424/423 |
| 2007/0032805 A1 | 2/2007 | Therin et al. | |
| 2007/0213522 A1* | 9/2007 | Harris et al. | 536/56 |
| 2008/0004657 A1* | 1/2008 | Obermiller et al. | 606/213 |

FOREIGN PATENT DOCUMENTS

| | | |
|---|---|---|
| EP | 1 535 631 | 6/2005 |
| EP | 1 953 174 | 8/2008 |
| WO | WO 2009/016518 | 2/2009 |

OTHER PUBLICATIONS

International Search Report PCT/IB2009/007742 dated Sep. 14, 2010.

* cited by examiner

*Primary Examiner* — Dianne Dornbusch

(57) ABSTRACT

The present invention relates to A bioresorbable implant comprising: a bioresorbable porous layer including a biopolymer foam and defining first pores, a bioresorbable porous three-dimensional mesh made from a microbial cellulose and defining second pores, wherein the bioresorbable porous layer is disposed in the bioresorbable porous three-dimensional mesh. The invention also relates to a method of making a bioresorbable implant.

17 Claims, 5 Drawing Sheets

MEDICAL IMPLANT INCLUDING A 3D MESH OF OXIDIZED CELLULOSE AND A COLLAGEN SPONGE

CROSS-REFERENCE TO RELATED APPLICATIONS

This application is a U.S. National Stage Application filed under 35 U.S.C. §371(a) of International Application No. PCT/IB2009/007742 filed Nov. 6, 2009, which claims the benefit of and priority to U.S. Provisional Application Ser. No. 61/112,306 filed Nov. 7, 2008, the entire contents of which are incorporated by reference herein.

The present disclosure relates to bioresorbable wall reinforcement implants that may be used, for example, in the repair, reinforcement or replacement of soft tissues, and to methods for preparing and using such medical devices. More particularly, a medical implant is provided which includes a bioresorbable porous matrix based on a biopolymer foam and defining first pores and a bioresorbable porous three-dimensional mesh obtained from microbial cellulose defining second pores, wherein the bioresorbable porous matrix is disposed in the bioresorbable porous three-dimensional mesh.

Permanent implants are not always essential for the repair, reinforcement or replacement of soft tissues. For example, in the case of treatment of certain defects such as for the treatment of hernias or reconstruction of a visceral wall, one may seek to limit the amount of foreign bodies which remain permanently in a human body and promote tissue reconstruction.

The structure of an implant for such uses should be favorable to cell growth and, at the same time, exhibit a threshold amount of mechanical strength in order to perform its reinforcement function. When an implant is bioresorbable, cell colonization should take place gradually and in a controlled manner, and at the same time in a homogeneous manner, as the implant degrades.

Such characteristics are difficult to achieve by microbial cellulose alone even if the microbial cellulose is a highly biocompatible material, showing unique properties which can help the repair, reinforcement or replacement of soft tissues.

Accordingly, there remains the need for an entirely bioresorbable implant which has sufficient mechanical properties while at the same time allowing effective, gradual and controlled cell growth, so that the tissue regeneration is accomplished effectively during the time the implant is effectively present in the human body, that is, before bioresorption of the implant.

The present disclosure relates to a bioresorbable wall reinforcement implant that may be used, for example, in the repair, reinforcement or replacement of soft tissues when a permanent implant is not necessary, e.g. treatment of hernias, reconstruction of a wall, such as a visceral wall. The implants according to the present disclosure may also be used in vitro as a tissue engineering product or support for culturing live cells.

In embodiments, a bioresorbable implant for the repair, reinforcement and replacement of soft tissues, is provided which includes 1) a bioresorbable porous matrix based on a biopolymer foam and defining first pores and 2) a bioresorbable porous three-dimensional ("3D") mesh obtained from microbial cellulose and defining second pores, wherein the bioresorbable porous matrix is disposed in the bioresorbable porous three-dimensional mesh, and the first and second pores are at least partially interconnected with one another.

In embodiments, the implant may also include a non-porous layer, as a barrier against the post-surgical adhesions.

The present disclosure relates to a bioresorbable implant comprising:
 a bioresorbable porous layer including a biopolymer foam and defining first pores,
 a bioresorbable porous three-dimensional mesh made from a microbial cellulose and defining second pores,
 wherein the bioresorbable porous layer is disposed in the bioresorbable porous three-dimensional mesh.

In embodiments, the first and second pores are at least partially interconnected with one another.

In embodiments, the bioresorbable implant further comprises a non-porous layer.

In embodiments, the microbial cellulose is derived from *Acetobacter xylinum* as wet pellicles or films. In embodiments, the microbial cellulose is oxidized.

In embodiments, the biopolymer foam includes pores having a size of from about 10 µm to about 500 µm. In embodiments, the biopolymer foam is made from a material selected from a natural, bioresorbable material. In embodiments, the biopolymer foam includes collagen. In embodiments, the biopolymer foam is from about 0.2 to about 1.5 cm thick. In embodiments, the porous layer has a density of from about 1 mg collagen/cm$^2$ to about 200 mg collagen/cm$^2$.

In embodiments, the bioresorbable implant further comprises a bioactive agent.

The present disclosure also relates to a method of making a bioresorbable implant, comprising:
 adding a solution of bioresorbable biopolymer to a bioresorbable porous three-dimensional mesh made from a microbial cellulose,
 lyophilizing the solution to create a bioresorbable foam layer in the bioresorbable porous three-dimensional mesh.

In embodiments, the solution of bioresorbable biopolymer comprises an aqueous acid solution or suspension of collagen at a concentration of about 2 g/l to about 100 g/l. In embodiments, the biopolymer foam layer is cross-linked.

In embodiments, the method further includes the step of applying a non porous layer to the bioresorbable porous three-dimensional mesh filled with the bioresorbable porous layer.

In embodiments, the non porous layer comprises a collagenic constituent.

The present disclosure also relates to a method of treating a wound comprising contacting a wound with the implant described above.

Various embodiments of the composite implant are described herein with reference to the drawings wherein.

Figure 1:
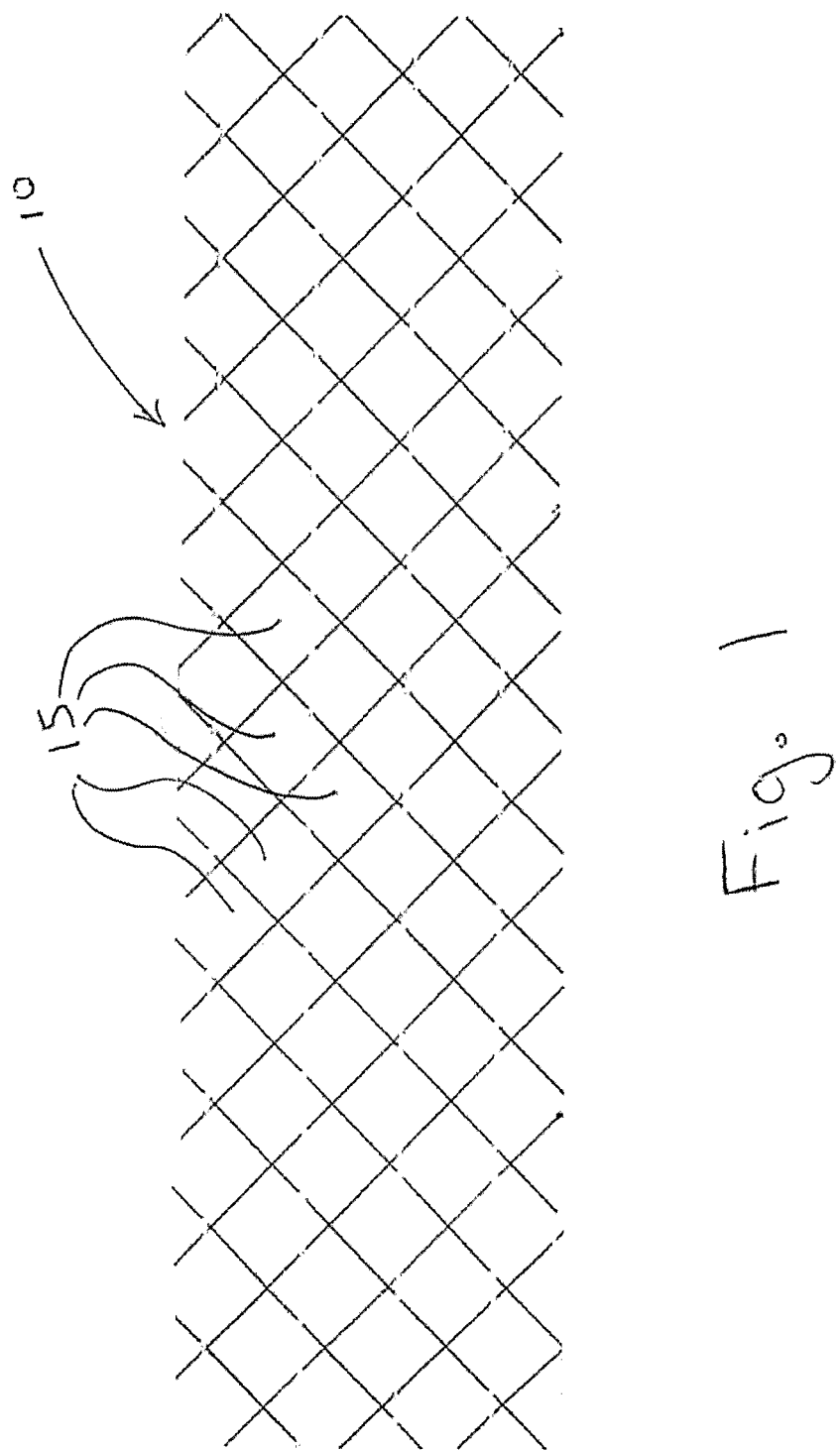
FIG. 1 is a schematic cross-sectional view of a mesh as described in at least one of the embodiments provided in the present disclosure.

For the purpose of the present disclosure, the term "implant" is intended to mean a biocompatible medical implant that can be implanted in the human or animal body.

For the purpose of the present disclosure, the term "bioresorbable" is intended to mean the characteristic according to which an implant and/or a material is degraded by the biological tissues and the surrounding fluids, in vivo after a given period of time, that may vary, for example, from one day to several months, depending on the chemical nature of the implant and/or of the material.

For the purpose of the present disclosure, the term "porous" is intended to mean the characteristic according to which a structure exhibits pores, or alternatively gaps, alveoli, holes or orifices, which are open, which may or may not be evenly distributed, and which promote all cell colonization.

For the purpose of the present invention, the term "foam" or "sponge" is intended to mean a porous structure with pores which may or may not be interconnected, obtained in particular by lyophilisation of a solution or suspension.

For the purpose of the present invention, the term "collagen" is intended to mean any known collagen of porcine, bovine or human origin, for example natural collagen, esterified collagen, such as methylated, ethylated or alternatively succinylated collagen, or one of its derivatives, which may or may not be heated, which may or may not be oxidized, or alternatively, for example, which may be crosslinked with another compound.

For the purpose of the present invention, the term "natural collagen" is intended to mean collagen which has not been chemically modified, other than a possible treatment with pepsin in order to digest the telemeric peptides.

For the purpose of the present invention, the term "non-denatured collagen" is intended to mean collagen which has not lost its helical structure.

Cellulose Mesh

Microbial cellulose possesses inherent characteristics which allow effective promotion of wound healing as described in U.S. Pat. No. 7,390,492, the entire content of which is hereby incorporated by reference. Microbial cellulose displays properties (such as unique multi-layer three dimensional laminar structures) that distinguish it from plant cellulose and other natural polymeric materials. Microbial cellulose shows excellent wet strength, does not easily breakdown under compression and demonstrates high moisture handling ability.

In the present disclosure, the microbial cellulose may be produced as wet pellicles or films from bacteria that synthesize cellulose. Cellulose is synthesized by bacteria belonging to the genera *Acetobacter, Rhizobium, Agrobacterium*, and *Sarcina*. Cellulose may be produced by certain bacteria from glucose in the presence of oxygen, (such as, for example, *Acetobacter xylinum*, referenced hereinafter as the "bacteria"), in static conditions or in a bioreactor (see, e.g. U.S. Pat. Nos. 4,912,049 and 5,955,326, the entire disclosures of which are incorporated herein by this reference). Cellulose suitable for use in the present implants may be obtained by the fermentation of the bacteria. In embodiments, a derivative of the cellulose is employed, such as oxidized cellulose resulting from the oxidation of the cellulose by periodic acid or nitrogen dioxide.

In embodiments, the cellulose mesh may be obtained by any method known in the art. For example, the bacteria are grown on or within a support as a mold that imparts porosity to the cellulose pellicle as it is formed and which is mechanically removed at the end of the fermentation process or which is degraded during the further steps of the cellulose purification and depyrogenation process. The open cellulose pellicle may be further packed down so as to increase its mechanical properties.

In other embodiments, the cellulose mesh is obtained from bacteria grown without a mold. The cellulose pellicles harvested at the end of the fermentation of the bacteria include a mesh formation step before, during or after the purification and depyrogenation process.

The pores may be obtained by any known techniques which may be suitable for the microbial cellulose, including, for example, by embossing, by mechanical perforation devices such as suitably arranged punching machines, or by methods involving the use of thermal or ultraviolet lasers operating in a frequency band such as to produce holes of the required size and distance apart in the cellulose sheet, via the use of vacuum, needle, water jet perforation or hot pins. The mesh formation step may be performed on wet or dry pellicles. Thus, in one embodiment, the final state of the cellulose mesh may be wet, and in other embodiments, the mesh may be dry.

The pores of the cellulose mesh can be from about 0.5 mm to about 5 mm, in embodiments from about 0.5 mm to about 3 mm.

The full thickness of the cellulose mesh may be from about 0.1 cm to about 3 cm, in embodiments from about 0.2 cm to 1 cm.

In embodiments, the cellulose mesh has all pores communicating from one side to the opposite side of the said mesh.

In other embodiments, the cellulose mesh has only some pores communicating from one side to the opposite side of the said mesh.

In other embodiments, the cellulose mesh has one porous side and the opposite side which is continuous and not macroporous (pores less than about 0.5 mm).

In embodiments, the microbial cellulose may be oxidized by periodic acid or by nitrogen dioxide at any step of the purification and depyrogenation process of the said cellulose. In one embodiment, the microbial cellulose may be oxidized when the cellulose is at least partly purified and depyrogenated. The final level of oxidation may be controlled in such a way as to get a suitable oxidation level available from several days to several months. In embodiments, the degree of oxidation may be in a range of from about 0.1 to about 0.9, in embodiments, in a range of from about 0.2 to about 0.65.

Other chemical modifications of cellulose for the generation of cellulose derivatives are also within the scope of the present disclosure. Cellulose belong to the family of biodegradable, renewable polymers that provides a broad range of important functional properties, and are thus widely used in industry today. However, some of the inherent properties of these polysaccharides limit their utility in certain applications. Therefore, native cellulose are commonly modified by physical, chemical, enzymic or genetic means in order to obtain specific functional properties, as described in for example, S. Richardson, L. Gorton/Analytica Chimica Acta, 2003; J. F. Kennedy, G. O. Phillips, D. J. Wedlock, P. A. Williams, Cellulose and its Derivatives: Chemistry, Biochemistry and Applications, Ellis Horwood, Chichester, 1985; A. Guilbot, C. Mercier, Starch, in: G. Aspinall (Ed.), The Polysaccharides, Academic Press, New York, 1985, the entire contents of each of which is hereby incorporated by reference. Native cellulose has an intrinsic lack of solubility in water and most organic solvent systems constitute a major obstacle for utilising cellulose in many industrial applications. It may be necessary to chemically derivatize cellulose in such a way to obtain derivatives soluble in organic solvents, for an easier remodelling of the microbial cellulose pellicles, for example.

In embodiments, the chemical modifications of cellulose may be based on reactions of the free hydroxyl groups in the anhydroglucose monomers, resulting in changes in the chemical structure of the glucose units and, ultimately, the production of cellulose derivatives. Suitable modifications involve esterification or etherification reactions of the hydroxyl groups with aliphatic halide derivatives.

According to the present disclosure, the microbial cellulose mesh may have sufficient mechanical properties for the repair, reinforcement or replacement of soft tissues. In embodiments, the microbial cellulose mesh shows a minimal elongation at break in at least one direction, measured according to ISO standard 13934-1 (properties of substances in tensile testing), of about 5 N, in embodiments, of about 20 N, and in other embodiments, of about 50 N.

The microbial cellulose mesh may also be designed in such a way that it can be easily fixed for surgeries, by any known techniques, such as suturing, stitching, stapling, tacking, and combinations thereof.

Biopolymer Foam

In the present application, the terms "porous layer" and "porous matrix" have the same meaning. The porous layer of the implant of the present disclosure includes a biopolymer foam.

In embodiments, the biopolymer foam of the implant has openings or pores over at least a portion of a surface thereof. In embodiments, the pores may be in sufficient number and size so as to interconnect across the entire thickness of the porous layer. In other embodiments, the pores may not interconnect across the entire thickness of the porous layer. Closed cell foams are illustrative examples of structures in which the pores may not interconnect across the entire thickness of the porous layer. In yet other embodiments, the pores do not extend across the entire thickness of the foam, but rather are present at a portion of the surface thereof. In embodiments, the openings or pores are located on a portion of the surface of the porous layer, with other portions of the porous layer having a non-porous texture. Those skilled in the art may envision other pore distribution patterns and configurations for the foam.

The foam of the present disclosure may be made from any suitable biocompatible natural or synthetic material. In embodiments, the material from which the foam is formed may be bioresorbable, non bioresorbable and combinations thereof. It should be understood that any combination of natural, synthetic, bioresorbable and non-bioresorbable materials may be used to form the porous layer.

Some examples of materials from which the foam may be made include, but are not limited to, poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

In embodiments, the foam may be formed from one or more bioresorbable, natural biological polymers. Suitable natural biological polymers include, but are not limited to, collagen, gelatin, cellulose, hydroxypropyl cellulose, carboxyethyl cellulose, chitin, chitosan, and combinations thereof. In alternate embodiments, the polymer constituent may be a polysaccharide such as chitin or chitosan, or polysaccharides modified by oxidation of alcohol functions into carboxylic functions such as oxidized cellulose. In embodiments, the natural biological polymers may be combined with any biocompatible synthetic materials to produce the porous layer of the implant.

The foam may be formed using any known method in the art suitable to forming a foam or sponge including, but not limited to, the lyophilization or freeze-drying of a composition. Suitable techniques for making foams are within the purview of those skilled in the art.

In embodiments, the foam may be at least about 0.1 cm thick, in embodiments from about 0.2 cm to about 1.5 cm thick. In embodiments, the porous layer may have a density of about 100 mg collagen/cm$^2$, in embodiments, from about 1 mg polymer/cm$^2$ to about 50 mg polymer/cm$^2$. In embodiments, the three dimensional density of the porous layer may be from about 5 mg collagen/cm$^3$ to about 200 mg polymer/cm$^3$, in embodiments from about 30 mg polymer/cm$^3$ to about 150 mg polymer/cm$^3$. In embodiments, the size of the pores in the foam may be from about 10 μm to about 500 μm.

In embodiments, the foam may be made from non-denatured collagen or collagen which has at least partially lost its helical structure through heating or any other known method, consisting mainly of non-hydrolyzed α chains, and having a molecular weight, in embodiments, of about 100 kDa. The collagen used for the porous layer of the present disclosure may be native collagen or atelocollagen, which may be obtained via pepsin digestion and/or after moderate heating as defined hereinabove. The origin and type of collagen may be as indicated for the non-porous layer described hereinbelow.

In embodiments, the collagen may be cured to any desired degree. The collagen suspension or solution may be made from non-cured, moderately cured, highly cured or extremely highly cured collagens or combinations thereof at any proportions. As used herein, the term "moderately cured" is intended to mean that the degradation of the porous layer will be at least about 90% complete (as measured by residual weight) by the end of about three weeks of implantation; the term "highly cured" is intended to mean that the degradation of the porous layer will be at least about 90% complete (as measured by residual weight) by the end of about three months of implantation; and the term "extremely highly cured" is intended to mean that the degradation of the porous layer will be at least about 90% complete (as measured by residual weight) by the end of about two years of implantation.

In embodiments, moderately cured collagen may be obtained by oxidative cleavage of collagen by periodic acid or one of its salts, as described hereinbelow for collagens of the non-porous layer.

In embodiments, highly cured collagen may be made from collagen cross-linked by glutaraldehyde or by any other known cross-linking agents such as, for example, but not limited to, isocyanates. The degree of crosslinking distinguishes between highly cured and very highly cured materials. Techniques for curing to various degrees are within the purview of those skilled in the art.

In embodiments, the collagen may optionally include non collagenic components, such as glycosaminoglycans, for example, but not limited to, chitosan. The glycosaminoglycans, in embodiments, display a degree of acetylation (DA) of from about 0.5% to about 50%, have a molecular weight ranging from about 100 g/ml to about 1,000,000 g/ml, and may display a low polydispersity index of from about 1.2 to about 1.8. In embodiments, the collagen may be a mixture of chitosans and other glycosamoniglycans, for example, but not limited to, hyaluronic acid, which have free amino groups capable of cross-linking to the oxidized collagen. In embodiments, the collagen suspension or solution may be a combination of oxidized collagen and chitosan which can form a cross-linked network.

In embodiments, the implant may be formed by pouring an aqueous acid solution or suspension of collagen at a concentration of about 2 g/l to about 100 g/l and an initial temperature of about 4° C. to about 25° C. over the cellulose mesh, which is therefore at least partly embedded in the suspension or solution. In embodiments, the concentration of collagen in the solution or suspension may be from about 10 g/l to about 100 g/l, in embodiments from about 20 g/l to about 80 g/l. In embodiments, the cellulose mesh may be freeze-dried, so as to produce a dry product.

In embodiments, the foam may be neutralized before freeze-drying as a solution or suspension, or after freeze-drying, under a dry form, at a pH of from about 6 to about 8. In embodiments, after pouring the solution or suspension of biopolymers in the cellulose mesh, the foam may be further cross-linked by any known cross-linking agents, i.e. glutaraldehyde, isocyanates, and/or by any physical treatment i.e., thermal processing, gamma- and beta-irradiation, after the foam is freeze-dried.

Non-Porous Layer

The implant of the present disclosure may include a non porous layer.

The non-porous layer may retard or prevent tissue ingrowth from surrounding tissues thereby acting as an adhesion barrier and preventing the formation of unwanted scar tissue. Thus, in embodiments, the non-porous layer possesses anti-adhesion properties and may be a physical barrier against microbial contamination.

In embodiments, when the cellulose mesh has a continuous, not macroporous side (see FIG. C), the non-porous layer may be the continuous, non macroporous side of the mesh itself.

In other embodiments, the non-porous layer of the present disclosure may be made from any biocompatible natural or synthetic material. The material from which the non-porous layer is formed may be bioresorbable, non-bioresorbable, and combinations thereof. It should be understood that any combination of natural, synthetic, bioresorbable and non-bioresorbable materials may be used to form the non-porous layer. Techniques for forming non-porous layers from such materials are within the purview of those skilled in the art and include, for example, but are not limited to, casting, molding and the like.

Some examples of materials from which the non-porous layer may be made include, but are not limited to, poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

In embodiments, natural biological polymers may be used in forming the non-porous layer of the implant. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, and combinations thereof. In addition, the natural biological polymers may be combined with any of the other polymeric materials described hereinabove to produce the non-porous layer of the implant.

In embodiments, an aqueous solution of a collagenic constituent is used to form the non-porous layer of the present disclosure. As used herein, the term "collagenic constituent" is intended to mean collagen which has at least partially lost its helical structure through heating or any other method, or gelatine. The term "gelatine" here includes commercial gelatine made of collagen which has been denatured by heating and in which the chains are at least partially hydrolyzed and having a molecular weight lower than about 100 kDa). The collagenic constituent used may be formed of non-hydrolyzed collagen, composed of α chains, and having a molecular weight of about 100 kDa. In the context of the present disclosure, "α chains" is intended to mean complete α chains or fragments produced by the loss of a small number of amino acids. The term "non-hydrolyzed" as used herein is intended to mean that less than 10% of the collagenic chains have a molecular weight below about 100 kDa. If heating is used to denature the helical structure of the collagen, the heating should be moderate and provided under gentle conditions so as to avoid degradation by hydrolytic cleavage of the gelatine thus formed.

Suitable collagen used in the present disclosure may be of human or animal origin, such as for example, type I porcine or bovine collagen, type I or type III human collagen, and/or mixtures thereof. Native collagen may be used, in acid solution or after processing, to eliminate the telopeptides, via pepsin digestion. The collagen may also be modified by oxidative cleavage using any technique known to those skilled in the art, including, but not limited to, the use of periodic acid or one of its salts as described by Tardy et al. in U.S. Pat. No. 4,931,546, the entire contents of which is hereby incorporated by reference. The technique involves mixing the collagen in acid solution with a solution of periodic acid or one of its salts at a concentration of from about $1 \times 10^{-5}$ M, in embodiments of from about $5 \times 10^{-3}$ M to about $1 \times 10^{-1}$ M, and at a temperature of from about 10° C. and 25° C. for about 10 minutes to about 72 hours. This process breaks down hydroxylysine and the sugars of the collagen, thus creating reactive sites without causing crosslinking. The oxidative cleavage of collagen allows moderate cross-linking in the collagenic material. In embodiments, oxidative cleavage may be provided by other means of moderate cross-linking, for example, but not limited to, beta or gamma irradiation. In embodiments, oxidative cleavage may be provided by other agents of moderate cross-linking, for example, but not limited to, chemical reagents at suitably low and non-toxic doses.

In other embodiments, the extent of collagen cross-linking can be increased by any techniques known to those skilled in the art to adjust the degradation time of the non-porous layer as desired. As used herein, the term "moderately crosslinked" is intended to mean that the degradation of the non-porous layer will be at least about 90% complete (as measured by residual weight) by the end of about three weeks of implantation; the term "highly crosslinked" is intended to mean that the degradation of the non-porous layer will be at least about 90% complete (as measured by residual weight) by the end of about three months of implantation; and the term extremely "highly crosslinked" is intended to mean that the degradation of the non-porous layer will be at least about 90% complete (as measured by residual weight) by the end of about two years of implantation.

In embodiments, a solution of oxidized collagen as defined hereinabove may be used to form the non-porous layer, having a collagen concentration of from about 5 g/l to about 50 g/l, in embodiments from about 25 g/l to about 35 g/l.

In embodiments, the solution of oxidized collagen may be heated, for example, to a temperature in excess of about 37° C., in embodiments to a temperature of from about 40° C. to about 50° C., for at least about one hour, to provide at least partial denaturing of the collagen's helical structure. Other physical or chemical techniques for denaturing collagen, includes but are not limited to, for example, ultrasonication, or the addition of chaotropic agents, and are within the purview of those skilled in the art.

In embodiments, at least one macromolecular hydrophilic additive that is chemically unreactive with the collagenic constituent may be added to the solution used to form the non-porous layer.

The macromolecular hydrophilic additive may have a molecular weight in excess of about 3,000 Daltons, in embodiments of from about 3,000 to about 20,000 Daltons. Suitable macromolecular hydrophilic additives include, but are not limited to, polyalkylene glycols (such as polyethylene glycol), polysaccharides (such as starch, dextran and/or cellulose), oxidized polysaccharides, mucopolysaccharides, and combinations thereof.

In embodiments, polyethyleneglycol 4000 (4000 corresponding to the molecular weight) may be added as a macromolecular hydrophilic additive. The concentration of hydrophilic additive(s) may be from about 2 to about 10 times less than that of the collagenic constituent. Optionally, the macromolecular hydrophilic additive may be eliminated by diffusion through the non-porous layer, in a few days.

Optionally, glycerine may be added to the solution used to form the non-porous layer. When present, the concentration of glycerine in the solution may be from about 2 to about 10 times less than that of the collagenic constituent, in embodiments, less than about one-third of the collagenic constituent concentration.

In embodiments, the concentrations of collagenic constituent, hydrophilic additive(s) and glycerine, when present, may be from about 2% to about 10% for the collagenic constituent, from about 0.6% to about 4% for the hydrophilic additive(s) and from about 0.3% to about 2.5% for glycerine, respectively.

The solution used to form the non-porous layer may be prepared by adding collagenic constituent, hydrophilic additive(s) and glycerine, when present, to water or a water/alcohol mixture, i.e., ethanol, at a temperature of from about 30° C. to about 50° C. The solution may be neutralized to a neutral pH to avoid hydrolyzing the collagenic constituent by heating and to obtain a film of physiological pH while permitting pre-cross-linking of the collagenic constituent if the mixture contains oxidized collagen as indicated hereinabove.

Optional Bioactive Agents

In embodiments, a bioactive agent may be combined with the implant and/or any of the individual components (the porous layer, the non-porous layer, a reinforcement member and/or a coating on a reinforcement member) used to construct the implant. In these embodiments, the implant can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively, a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the medical implant in any suitable form of matter, e.g., films, powders, liquids, gels and the like.

Suitable examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, enzymes and combinations thereof.

Anti-adhesive agents can be used to prevent adhesions from forming between the implantable medical implant and the surrounding tissues opposite the target tissue. In addition, anti-adhesive agents may be used to prevent adhesions from forming between the coated implantable medical implant and the packaging material. Suitable anti-adhesive agents include, but are not limited to, poly(vinyl pyrrolidone), carboxymethyl cellulose, hyaluronic acid, polyethylene oxide, poly vinyl alcohols and combinations thereof.

Antimicrobial agents may be included as a bioactive agent in a bioactive coating and/or in film layers to reinforce the antimicrobial properties of the implant of the present disclosure. Suitable antimicrobial agents include, but are not limited to, triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, biocide quaternary ammonium salts such as dimethyl diallyl ammonium chloride (DADMAC) and its derivatives, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B and antimicrobial polysaccharides such as fucans and derivatives and oligomers of chitosan may be used as a bioactive agent in the bioactive coating.

Other bioactive agents which may be used as a bioactive agent in a coating composition and/or in a film layer composition include, but are not limited to, local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; immunological agents; and combinations thereof.

Other suitable bioactive agents which may be included in a coating composition and/or in a film layer composition include, but are not limited to, viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ((3-IFN, (a-IFN and y-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; ribozymes; and combinations thereof.

Assembling the Non Porous Layer to the Cellulose Mesh Filled with the Foam

Figure 2:
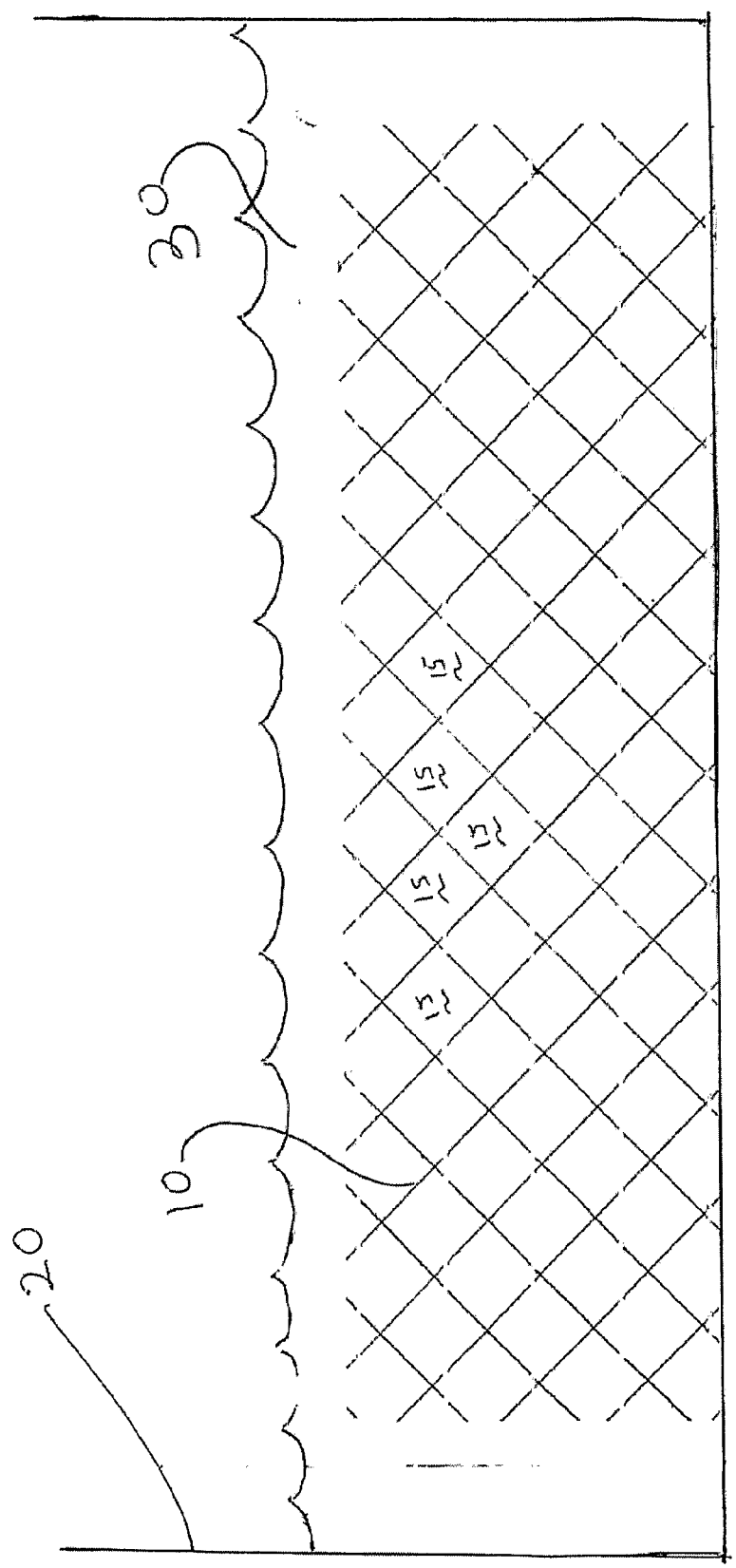
FIG. 2 is a schematic cross-sectional view of a mesh placed in a vessel as described in at least one of the embodiments provided in the present disclosure.
Figure 3:
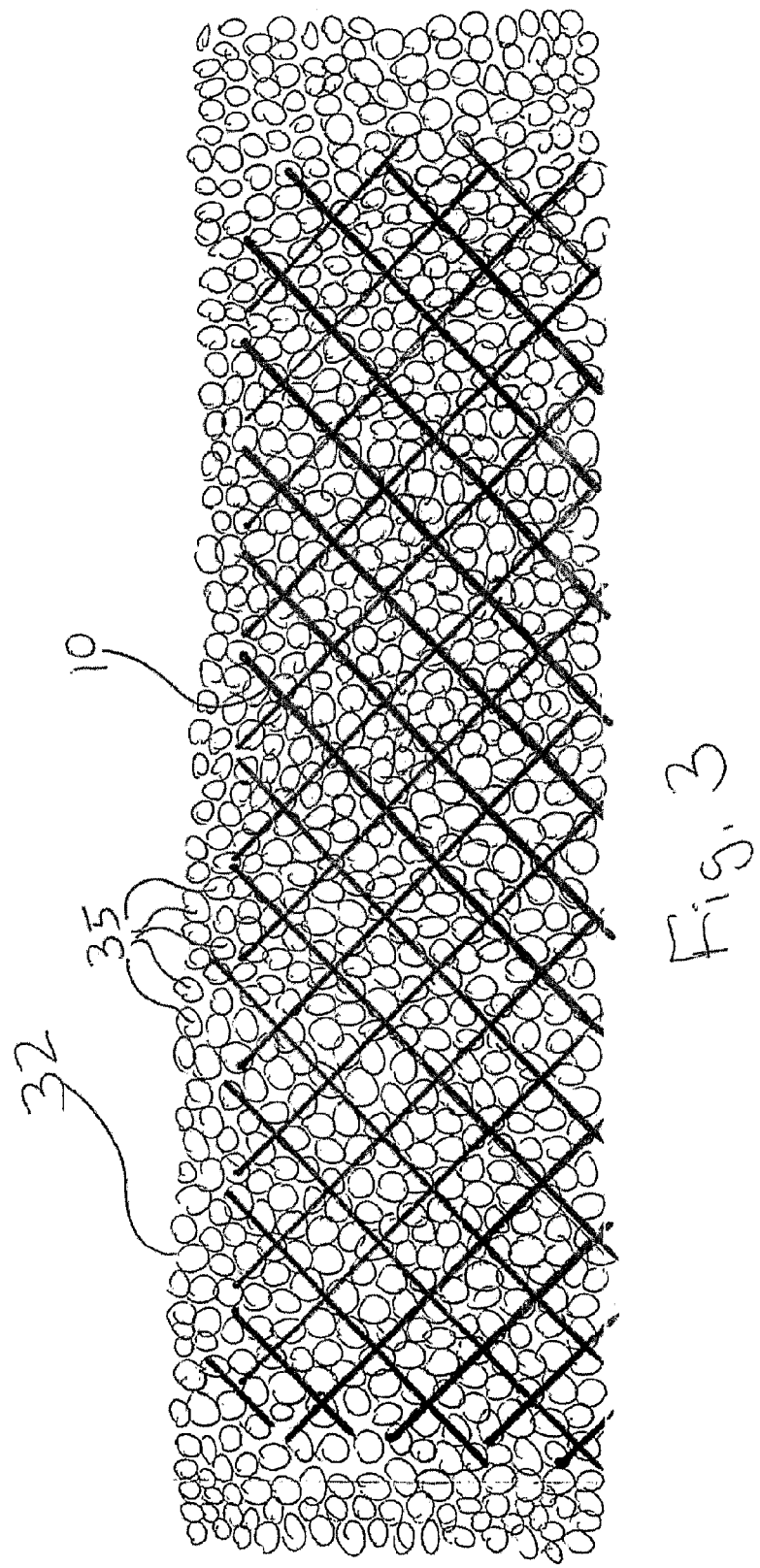
FIG. 3 is a schematic cross-sectional view of a bioresorbable implant as described in at least one of the embodiments provided in the present disclosure.

A cellulose mesh is filled with foam as described above. In embodiments, as shown schematically in FIGS. 1-3, a cellulose mesh 10 defining first pores 15 (see FIG. 1) is placed within a vessel 20 and the vessel is filled with a solution 30 destined to form the foam (see FIG. 2). After the solution gels, it is lyophilized to produce foam 32 defining second pores 35 within mesh 10 as shown in FIG. 3.

In embodiments, the non porous layer which is not a part of the cellulose mesh may be prepared by first pouring a solution of collagenic constituent, destined to form a film, and optionally containing the hydrophilic additive(s) and glycerine, onto an adequate, substantially flat support or substrate and distributing it evenly.

The support is inert in that it does not react with the components of the present disclosure and is not involved in the cross-linking process. In embodiments, the support may be made from a hydrophobic material such as, for example, PVC or polystyrene, or a strippable material which will remain slightly adhesive and which can then be separated from the implant at the time of surgical use. In embodiments, the support may consist of a film, for example, dried collagen, onto which the solution is poured, or a layer of collagenic material gel in a distinctly more advanced state of gelification.

In embodiments, the density of the thin layer initially applied as a solution to the substrate may be from about 0.1 g solution/cm² to about 0.3 g solution/cm². This collagenic solution may be poured at a temperature of from about 4° C. to about 30° C., in embodiments of from about 18° C. to about 25° C. Once applied to the substrate, the collagen solution is allowed to form a gel, until the solution is no longer fluid like, for about 30 min, as the gel is poured under a laminar flow hood. Gelling results from cooling of the collagen solution.

Figure 4:
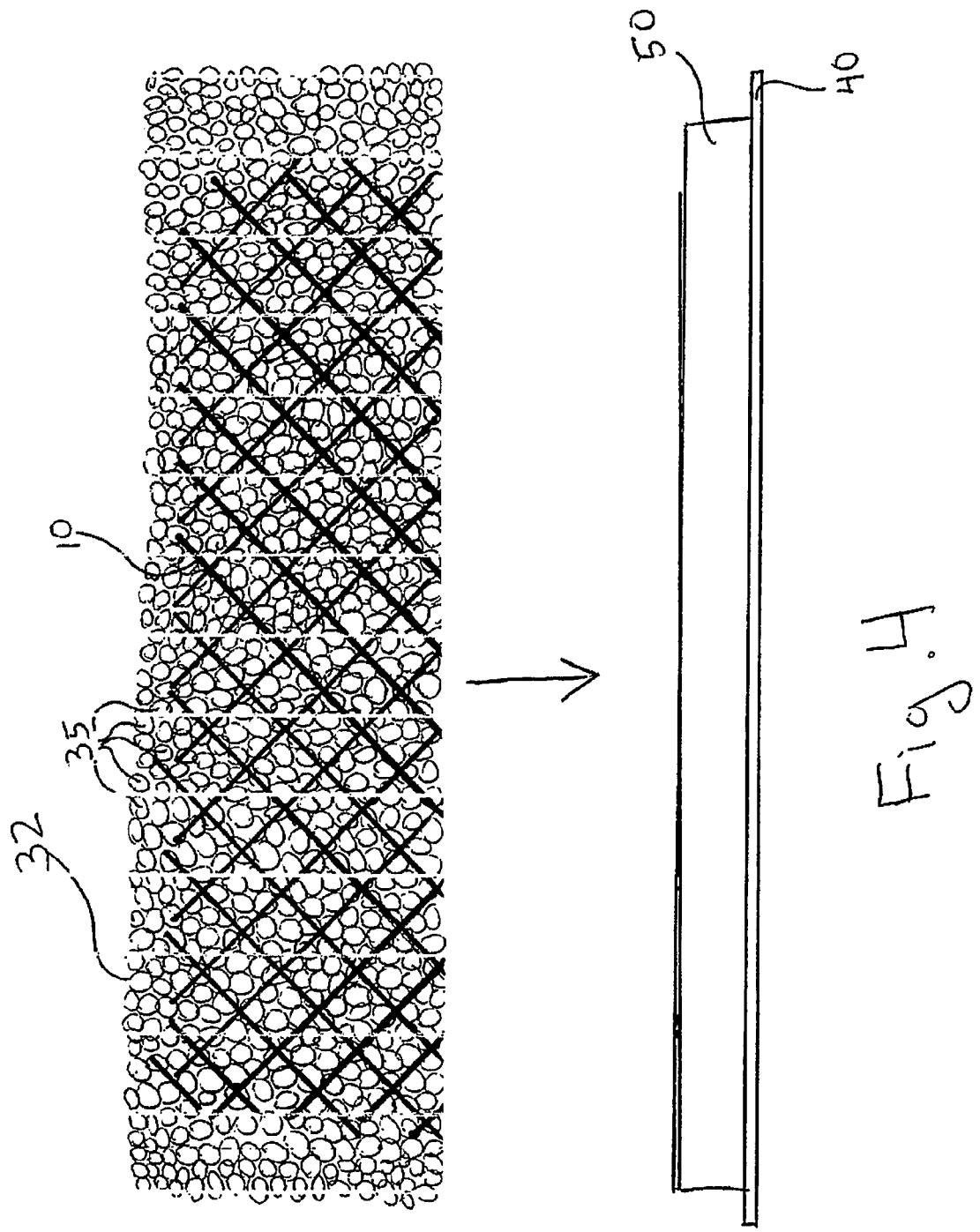
FIG. 4 is a schematic cross-sectional view of the bioresorbable implant of FIG. 3 being combined with a solution; and, FIG. 5 is a schematic cross-sectional view of a bioresorbable implant as described in at least one of the embodiments provided in the present disclosure.

The cellulose mesh 10 filled with the foam 32 is then applied to the solution 50 upon substrate 40 as shown schematically in FIG. 4. Application of the cellulose mesh means simply laying the cellulose mesh onto the gelled solution, and optionally applying slight pressing. The pressing should be insufficient to cause any significant disruption of the portion of the layer of solution in contact with the substrate thereby helping to maintain the integrity and anti-adhesion characteristics of the non-porous layer. The pressing may leave the surface of the cellulose mesh exposed at the surface of the solution.

Following application of the cellulose mesh, but before complete gelification of the collagen solution, the resulting composite implant is dried in order to obtain the final implant. When the collagenic solution destined to form a film includes oxidized collagen, it is polymerized while the material is drying at a temperature of from about 4° C. to about 30° C., in embodiments from about 18° C. to about 25° C. In other embodiments, the implant is further processed by adding a second non-porous layer on the other side. The material may be dried in a jet of sterile air.

After drying, the composite implant can be separated from its support, trimmed to size as necessary, packaged and sterilized using conventional techniques, such as, but not limited to, irradiation with beta (electronic irradiation) or gamma (irradiation using radioactive cobalt) rays. In embodiments where hydrolytically unstable materials are used in forming the composite, such as polyglycolic acid or polylactic acid, the composites are packaged under sufficiently dry conditions to ensure that no degradation of the composite takes place during storage.

Figure 5:
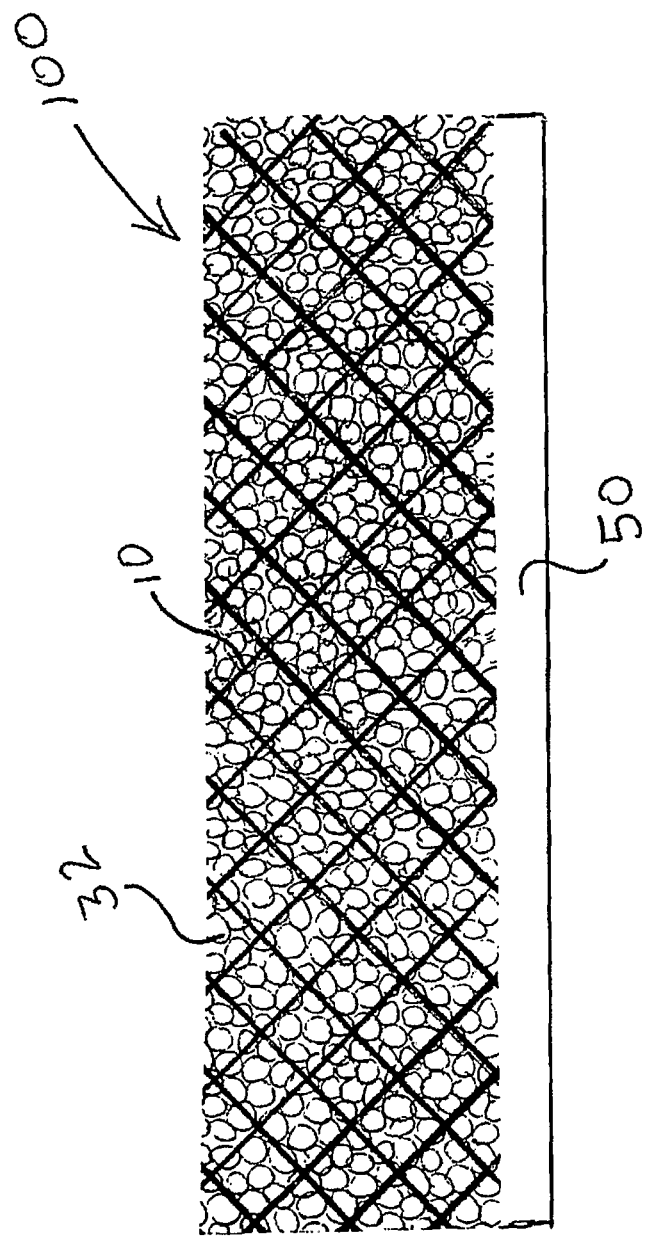

As seen schematically in FIG. 5, implant 100 includes cellulose mesh 10 filled with foam 32 and non-porous film 50.

The medical implants of the present disclosure are stable at ambient temperature and remain stable to be handled at temperatures which may rise to temperatures of from about 37° C. to 40° C. The thickness of the non-porous layer may be less than about 100 µm thick, in embodiments, from about 30 µm to about 75 µm thick. The thickness of the porous layer may be from about 0.2 cm to about 1.5 cm thick, in embodiments from about 0.3 cm to about 1.2 cm thick. The medical implants in accordance with this disclosure may be produced at a predetermined size or produced in large sheets which may be cut to sizes appropriate for the envisaged application.

The medical implants of the present disclosure may be implanted using open surgery or in a laparoscopic procedure. When implanted laparoscopically, the composite implant should be rolled with the porous side on the inside before trocar insertion. The porous layer may act as a long lasting support of the repair and/or regeneration of any soft tissues. The implants described herein are also suitable for preventing post-operative adhesion, particularly in bleeding wounds, because the film prevents adherence. The non-porous layer also protects the healing wound for several days as it forms a barrier to bacteria and micro-organisms.

The medical implant of the present disclosure may maintain one or more of the original and unique properties of bacterial cellulose sheets such as high biocompatibility, extreme hydrophilicity, unique multi-layered three dimensional laminar structures which provide its moisture handling properties, excellent wet strength, high resistance to breakdown under compression, conformability, absence of generation of harmful particles of the cellulose mesh after rubbing against surrounding tissues or erosion at sharp edges of cartilage and bones, while including a sponge made from polymers, and enhancing the healing process of soft tissue defects.

The medical implant of the present disclosure may allow the cell colonization to take place gradually and in a controlled manner, and at the same time in a homogeneous manner, as the implant degrades, when implanted, therefore optimizing the repair, reinforcement or replacement of soft tissues, by providing a fully biocompatible sponge associated with the bacterial cellulose mesh. Moreover, the medical implant of the present disclosure reduces post surgical adhesions when the implant is covered with the non porous layer.

It will be understood that various modifications may be made to the embodiments disclosed herein. Thus, those skilled in the art will envision other modifications within the scope and spirit of the disclosure.

We claim:

1. A bioresorbable implant comprising:
a bioresorbable porous layer including a biopolymer foam defining first pores, and a three-dimensional density from about 30 mg collagen/cm$^3$ to about 150 mg collagen cm$^3$,
a bioresorbable porous three-dimensional mesh made from a microbial cellulose having a thickness of about 0.1 cm to about 3 cm, and defining second pores from about 0.5 mm to about 5 mm, wherein the bioresorbable porous layer is disposed in the bioresorbable porous three-dimensional mesh, and
a non-porous film applied to the bioresorbable porous three-dimensional mesh including the bioresorbable porous layer.

2. The bioresorbable implant of claim 1, wherein the first and second pores are at least partially interconnected with one another.

3. The bioresorbable implant of claim 1, wherein the microbial cellulose is derived from Acetobacter xylinum as wet pellicles or films.

4. The bioresorbable implant of claim 1, wherein the microbial cellulose is oxidized.

5. The bioresorbable implant of claim 1, wherein the biopolymer foam comprises pores having a size of from about 10 μm to about 500 μm.

6. The bioresorbable implant of claim 1, wherein the biopolymer foam is from about 0.2 to about 1.5 cm thick.

7. The bioresorbable implant of claim 1, further comprising a bioactive agent.

8. The bioresorbable implant of claim 1, wherein the microbial cellulose mesh displays a minimal elongation at break in at least one direction of about 50 N.

9. The bioresorbable implant of claim 1, wherein the microbial cellulose has a thickness of about 0.2 cm to about 1 cm.

10. The bioresorbable implant of claim 1, wherein the non-porous film is positioned on a first side of the implant to reduce postsurgical adhesions and the porous layer is positioned on a second side opposite the first side of the implant to allow for cell colonization.

11. The bioresorbable implant of claim 1, wherein the non-porous layer is from about 30 μms to about 75 μms thick and the porous layer is from about 0.3 cms to about 1.2 cms thick.

12. A method of making a bioresorbable implant, comprising:
adding an aqueous acid solution or suspension of collagen to a bioresorbable porous three-dimensional mesh made from a microbial cellulose having a thickness of about 0.1 cm to about 3 cm, and defining second pores from about 0.5 mm to about 5 mm,
lyophilizing the solution to create a bioresorbable foam layer in the bioresorbable porous three-dimensional mesh, wherein the bioresorbable foam layer includes a three-dimensional density from about 30 mg collagen/cm$^3$ to about 150 mg collagen/cm$^3$, and
applying a non porous layer to the bioresorbable porous three-dimensional mesh that has been filled with the bioresorbable foam layer.

13. The method of claim 12, wherein the biopolymer foam layer is cross-linked.

14. The method of claim 12, wherein the non porous layer comprises a collagenic constituent.

15. The method of claim 12, wherein the microbial cellulose has a thickness of about 0.2 cm to about 1 cm.

16. The method of claim 12, wherein the non-porous film is positioned on a first side of the implant to reduce postsurgical adhesions and the porous layer is positioned on a second side opposite the first side of the implant to allow for cell colonization.

17. The method of claim 12, wherein the non-porous layer is from about 30 μmsto about 75 μms thick and the porous layer is from about 0.3 cms to about 1.2 cms thick.

* * * * *